(12) United States Patent
Low et al.

(10) Patent No.: US 7,685,883 B2
(45) Date of Patent: Mar. 30, 2010

(54) ANALYTIC SINTERING FORMS AND METHOD FOR USING SAME

(75) Inventors: Steven C. Low, Mesa, AZ (US); Neal W. Muylaert, Apache Junction, AZ (US)

(73) Assignee: The Boeing Company, Chicago, IL (US)

( * ) Notice: Subject to any disclaimer, the term of this patent is extended or adjusted under 35 U.S.C. 154(b) by 347 days.

(21) Appl. No.: 11/601,052

(22) Filed: Nov. 17, 2006

(65) Prior Publication Data

US 2008/0115586 A1   May 22, 2008

(51) Int. Cl.
*G01N 3/00* (2006.01)
(52) U.S. Cl. ........................................ 73/788
(58) Field of Classification Search ............... 73/788, 73/786
See application file for complete search history.

(56) References Cited

U.S. PATENT DOCUMENTS

| | | | | |
|---|---|---|---|---|
| 3,809,545 A | * | 5/1974 | Benjamin | 75/255 |
| 3,994,428 A | * | 11/1976 | Li | 228/18 |
| 4,705,560 A | * | 11/1987 | Kemp et al. | 75/342 |
| 5,581,039 A | * | 12/1996 | Yasutomi et al. | 73/768 |
| 5,745,834 A | | 4/1998 | Bampton et al. | |
| 6,946,180 B2 | * | 9/2005 | Hawkins | 428/67 |
| 7,034,246 B2 | | 4/2006 | Muylaert et al. | |
| 7,316,722 B2 | * | 1/2008 | Komori et al. | 55/523 |
| 2006/0243057 A1 | * | 11/2006 | Bailey et al. | 73/788 |

* cited by examiner

*Primary Examiner*—Lisa M Caputo
*Assistant Examiner*—Octavia Davis
(74) *Attorney, Agent, or Firm*—Tung & Associates

(57) ABSTRACT

A set of analytic forms provide empirical data used to determine the material properties of a part following its fabrication. Multiple of families of the forms are identically processed to provide a variety of data, including the reaction of the part material to compression, tension and bending stresses. The forms in each family have a structural feature that singularizes the directional effect of gravity on a test cross section of the material. The dimensions of the test cross section progressively vary within each family so that data can be generated for multiple levels of stress.

9 Claims, 4 Drawing Sheets

ANALYTIC SINTERING FORMS AND METHOD FOR USING SAME

BACKGROUND OF THE INVENTION

1. Field of the Invention

This invention broadly relates to analytical tools and techniques for evaluating manufacturing processes, and deals more particularly with analytic forms used to evaluate part designs, materials and processes, especially those involving powder metal.

2. Description of the Related Art

The properties of a manufactured part, such as powder metal part, often depend on the materials and processes used to manufacture the part, as well as the part design. Powder part metallurgy is a forming and fabrication technique comprising three primary processing stages. First, the primary material is physically divided into many small individual particles. Next, the powder is formed to produce a structural shape near the true shape and dimensions of the object ultimately to be manufactured. Finally, the end part is solidified in a radiant thermal, microwave or ultrasonic furnace by applying pressure or vacuum, high temperature, microwave, or sonic energy, or any combination thereof during which self-welding among the powder particles occurs. The end product is a useful metallic part in net or near net shape that exhibits favorable material properties of the parent powder material.

Both the dimensions and other mechanical properties of powder metal parts may be affected by a variety of processing parameters such as molding pressures/times, sintering temperature, curing period etc. Accordingly, it is desirable to observe the part at each stage of the manufacturing process in order to develop information about process controls and the materials that can be used to make adjustments in order to improve part quality. It is impractical, however, to observe the reaction of the powder metal part during the sintering process for example, because sintering is normally performed within a furnace where it may not be possible to directly monitor or observe the part. In addition, it is desirable to have a means of performing comparative analyses on parts that yield data for mechanical properties of the powder material during all phases of the sintering process.

Accordingly, there is a need for an analytical tool that can be used to develop data reflecting the behavior of the powder metal during the manufacturing process, which can then be used to optimize material selection, part design and process guidelines. The present invention is directed toward satisfying this need.

BRIEF SUMMARY OF THE INVENTION

In accordance with one aspect of the invention, analytic structures are provided for use in analyzing a process to manufacture a part, comprising at least one family of analytical forms manufactured by the process, the forms having a common structural feature that is subjected to stress during the manufacturing process. The structural feature of the forms have differing cross sectional areas such that the structural feature of each form is subjected to a different degree of stress during the manufacturing process. Each of the analytical forms includes an identical mass acting on a corresponding structural feature for applying stress to the feature. The analytical forms may be formed from powder metal using the same process used to manufacture the part. The forms may be configured such that the stress imposed on the structural feature comprises one of a compressive stress, bending stress, shear stress or tension stress. The mass is arranged so that the force of gravity generates the stress through the cross sectional area of the structural feature.

In accordance with another aspect of the invention, an analytical tool is provided for use in analyzing a process for producing powder metal parts. The tool comprises at least a first family of powder metal forms produced by the process, wherein the forms are respectively subjected to different levels of stress during the process and provide at least a first set of data that is predictive of the mechanical properties of the powder metal parts produced the process. The powder metal forms have differing cross sectional areas, and an identical mass that imposes stress on the cross sectional area of the associated form.

In accordance with still another aspect of the invention, a method is provided for analyzing a process used to manufacture a powder metal part, comprising the steps of: using the process to produce a family of powder metal analytical forms; measuring physical properties of common features of each of the forms in the family; comparing the measured properties of each form with the measured properties of the other forms in the family; and, predicting the material properties of the part based on the results of the comparison. The features are preferably formed so as to singularize the direction of gravity on a cross sectional area of the feature. Measuring of the physical properties may include measuring the effect of stress on the common features.

The invention provides an efficient means for gathering both quantitative and comparative data regarding the selection of materials and processes that are useful in developing guidelines for designing powder metal parts. The analytic forms can be analyzed to generate empirical data in order to quantify the mechanical properties and behavior of the powder metal material during the manufacturing process.

These and other features, aspects and advantages of the invention will become better understood with reference to the following drawings, description and claims.

DETAILED DESCRIPTION OF THE INVENTION

Figure 1:
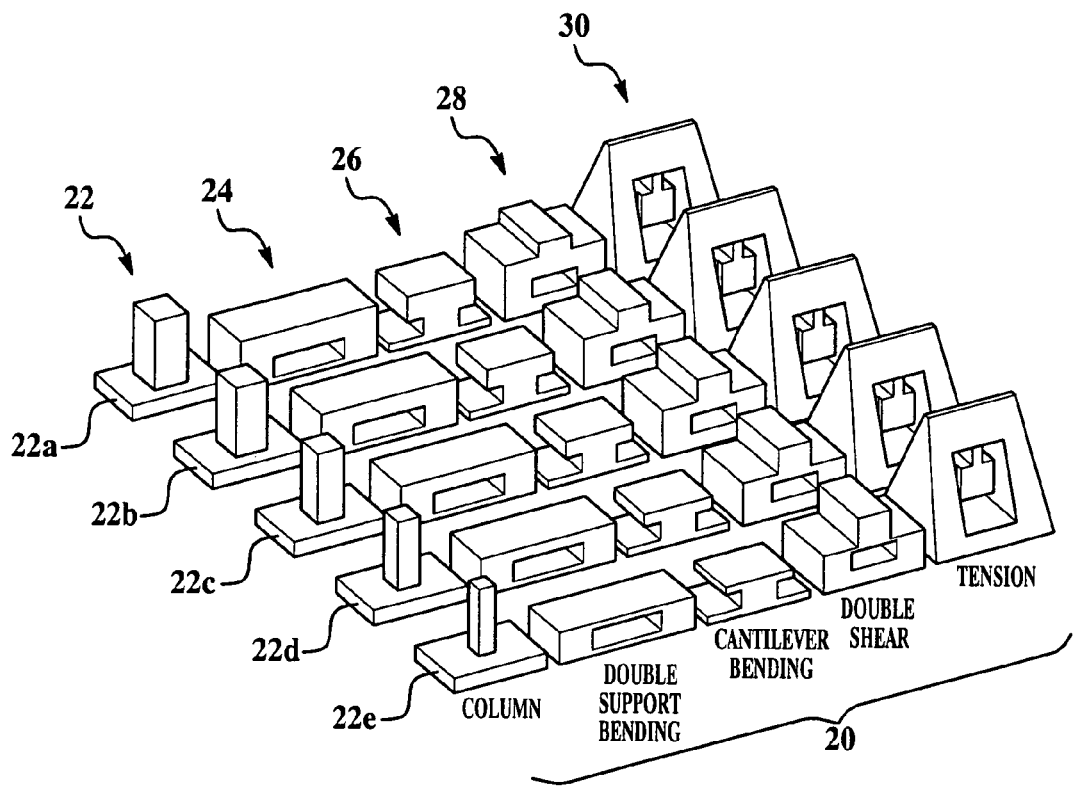
FIG. 1 is a perspective view of a set of analytic forms in accordance with the present invention.

Referring first to FIG. 1, the invention relates to a set 20 of analytic forms used to develop data that can be employed to perform comparative material property analysis during any phase or cycle of the process that is used to produce the forms. In the illustrated example, the set 20 of forms comprises five families 22, 24, 26, 28, 30 of forms, each of the families having five members. For example, the family 22 includes five forms 22*a*, 22*b*, 22*c*, 22*d*, 22*e*. As will be discussed later in more detail, each of the families 22-30 is used to develop information relating to specific mechanical properties of the powder metal material from which the forms are manufactured. Family 22, for example, employs a column as a structural feature used to generate information about the materials when subjected to compression stress. The forms in family 24 provide comparative data relating to how the material responds to different levels of bending stresses when supported at two points. The forms in family 26 provide comparative data indicating how the material responds to different levels of bending stress when supported in a cantilever manner. The forms in family 28 provide comparative data revealing how the material responds to different levels of shear stresses, while family 30 can be used to generate comparative data revealing how the material responds to different levels of tension stresses.

As will be discussed below, the analytic forms in each of the families 22-30 have specific shapes and structural features that singularize the directional effect of gravity through specific test cross sections in order to allow tensile, shear and compressive data to be gathered, and to allow comparative material property analysis during any phase or cycle of the sintering process. The analytic forms are made of the same powder material and are processed in the same manner as a part to be designed and manufactured using the process, in order to provide actual empirical data. This empirical data can then be used to evaluate the behavior of the material during the various stages of the manufacturing process.

By analyzing the behavior of the material, certain predictions may be made regarding the design of parts and the incorporation of guidelines into the designed process. After processing is complete, the analytic forms in each family 22-30 may be scrutinized for failure, deflection, slump, cross-sectional coning, metallurgic grain structure and other desired analytic tests relating to metallurgy, material properties, process variance or geometric variance. Additionally, the data gathered for each form in a family 22-30 is compared with the data gathered for the other forms in the same family in order to determine how the material responds to different levels of applied stress.

As previously indicated, the analytic forms are produced in the same manner using the same manufacturing process used to produce a finished part. These processes may include, but are not limited to molding, extruding, additive deposition, subtractive machining, casting, pressing, compaction, and rolling, all with or without the use of adjunct binders. The specific behavior (failure, slump, sag, etc) of the analytic forms, and comparison of the form to the other forms within its respective family 22-30, may provide empirical evidence that can be used to quantify the mechanical properties and behavior of the material used to produce the analytic form during the process it was subjected to.

The geometric design of each analytical form within each family 22-30 singularizes the directional effect of gravity on a body of known mass and dimension through specific test cross sections that subject the material within the target cross section to substantially only tensile, shear or compressive stress. As used herein, "target cross section" means a cross sectional area taken through a particular structural feature of a form that is specifically configured to singularize the directional effect of gravity on the feature.

Figure 2:
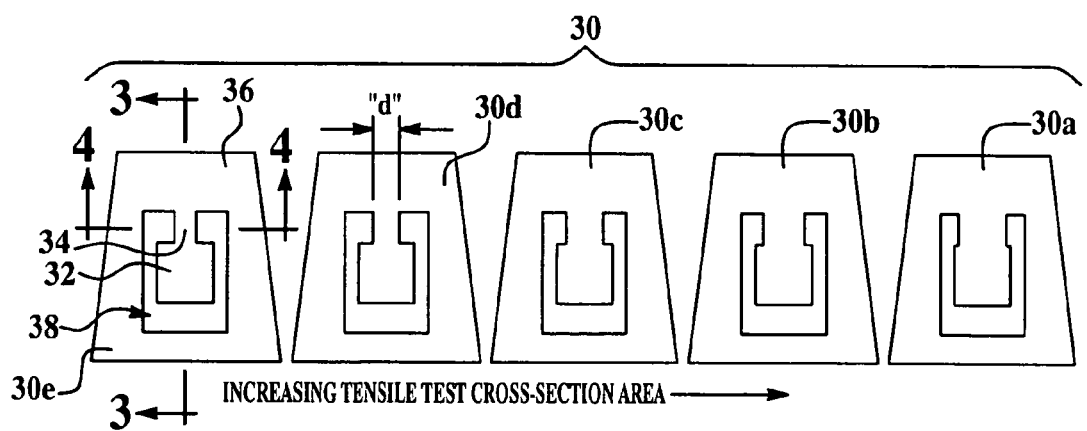
FIG. 2 is a front elevational view of one family of forms shown in FIG. 1, useful in developing data related to tension properties.
Figure 3:
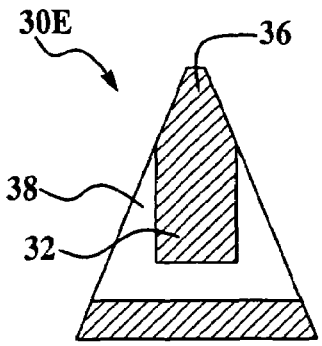
FIG. 3 is a sectional view taken along the line 3-3 in FIG. 2.
Figure 4:
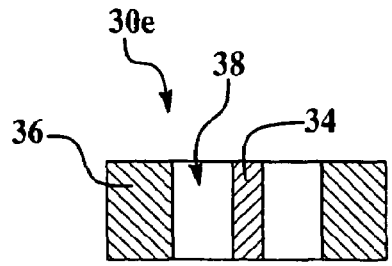
FIG. 4 is a sectional view taken along the line 4-4 in FIG. 2.

Attention is now directed to FIGS. 2-4 depicting the family 30 of analytic forms 30*a*-30*e* which may be used to develop information revealing the reaction of the powder metal material to tension stress. Examples of manufactured parts that benefit from this type of information include overhanging elements, bosses, flanges and, and other parts. The forms 30*a*-30*e* each include a main body portion 36 having a central open area 38 within which a mass 32 is suspended from the body 36 by a structural element 34 having a rectangular target cross section, as best seen in FIG. 4. The width of the target cross section of the structural element 34 is designated as "d", and as shown in FIG. 2 the width "d" progressively increases such that analytic form 30*a* has a maximum value for the dimension "d" and form 30*e* possesses the smallest value of "d", within the family 30. The central axis of the structural element 34 and the mass 32 are aligned so that the entire target cross section of the structural element 34 is subjected substantially to tensile stress in proportion to the supported mass 32 and the target cross sectional area of the particular form 30*a*-30*e*. It should be noted here that although the structural feature 34 is supported by the body 36, feature 34 could be supported by an accompanying artifact separate from the analytic form 30*a*-30*e*.

Figure 5:
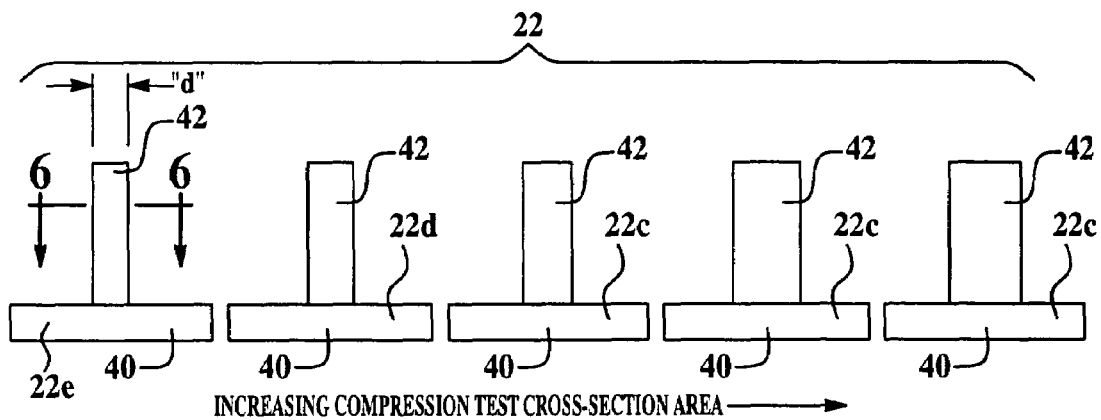
FIG. 5 is a front elevational view of another family of analytic forms shown in FIG. 1, useful in developing information relating to compression properties.
Figure 6:
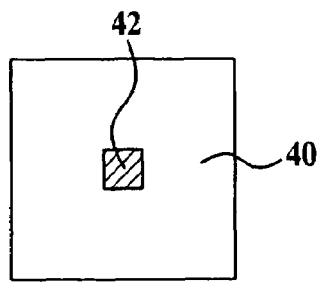
FIG. 6 is a sectional view taken along the line 6-6 in FIG. 5.

Referring now to FIGS. 5 and 6, family 22 of analytic forms 22*a*-22*e* are configured to provide empirical information describing the behavior of the material relating to compressive failure, coning and column instability. Forms 22*a*-22*e* each comprise a generally square base 40 having a column 42 positioned in the center of the base 40. The column 42 forms a structural feature that provides both the test mass and cross sectional test area used to determine the mechanical properties of the material when subjected to compressive stress. The target cross section of the column 42 is square, with each side having a dimension "d" that increases progressively, from form 22*e* to 22*a*.

Figure 7:
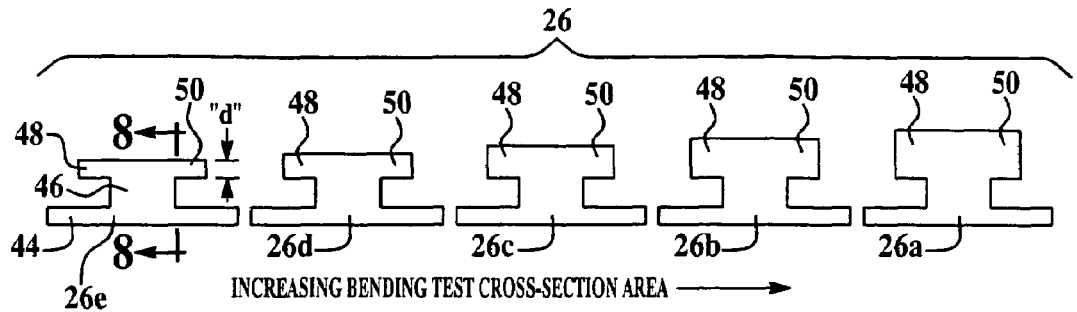
FIG. 7 is a front elevational view of another family of analytic forms shown in FIG. 1, useful in developing information relating to bending stress properties.
Figure 8:
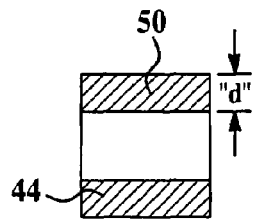
FIG. 8 is a sectional view taken along the line 8-8 in FIG. 7.

Reference is now made to FIGS. 7 and 8 depicting the details of the analytic forms 26*a*-26*e* of family 26. The forms in family 26 can be analyzed to provide empirical data revealing the behavior of the material in response to bending stress and modulus. Examples of manufactured parts that benefit from this type of information include flanges, overhanging elements, and other parts. The forms 26*a*-28*e* each comprises a generally rectangular base 44 and a central column 46. Two portions 48, 50 of material overhang the sides of the column 46, each having a thickness "d" which progressively increases from form 26*e* to form 26*a*. The overhanging portions 48, 50 form structural features supported by the central column 46 that subjects the target cross sectional area of features 48, 50 (best seen in FIG. 8) to bending stress and shear stress in proportion to the mass of the features 48, 50, and the area of the target test cross section. As previously indicated, the behavior of the material forming the cavaliered structural features 48, 50 provides information related to tensile/bending failure, and bending modulus.

Figure 9:
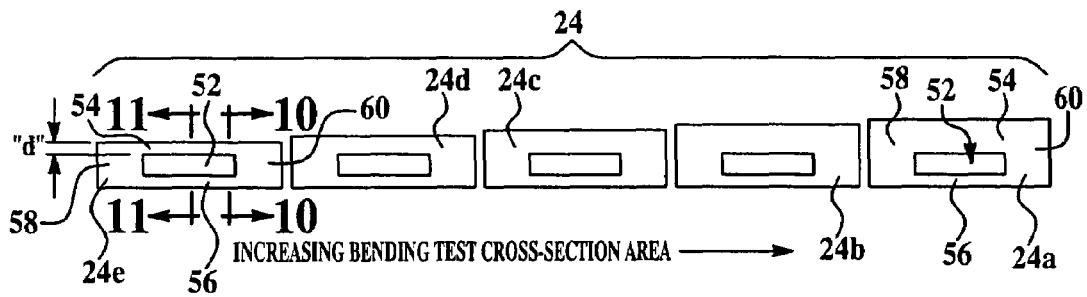
FIG. 9 is a front elevational view of another family of analytic forms shown in FIG. 1, useful in developing information relating to tensile/bending failure and bending modulus.
Figure 10:
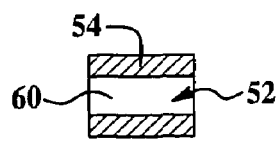
FIG. 10 is a sectional view taken along the line 10-10 in FIG. 9.
Figure 11:
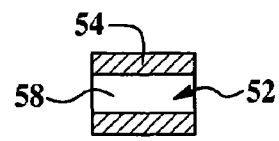
FIG. 11 is a sectional view taken along the line 11-11 in FIG. 9.

Referring now to FIGS. 9-11, family 24 can be used to develop empirical information revealing the behavior of the material related to tensile/bending failure, and bending modulus. Examples of manufactured parts that benefit from this type of information include bridging elements, caps, flanges, elements enclosing cavities, and other parts. Each of the forms 24a-24e comprises a base 56, a pair of spaced apart columns 58, 60 and a structural feature in the form of a bridging portion 54 that is supported at its opposite ends by columns 58, 60. A central area 52 of the forms 24a-24e is open so that the sole support of the structural feature 54 is the columns 58, 60. The thickness of the bridging portion 54 is designated as "d" which increases progressively in value from form 24e to form 24a. Thus, the test target cross sectional area increases progressively from form 24e to form 24a.

Figure 12:
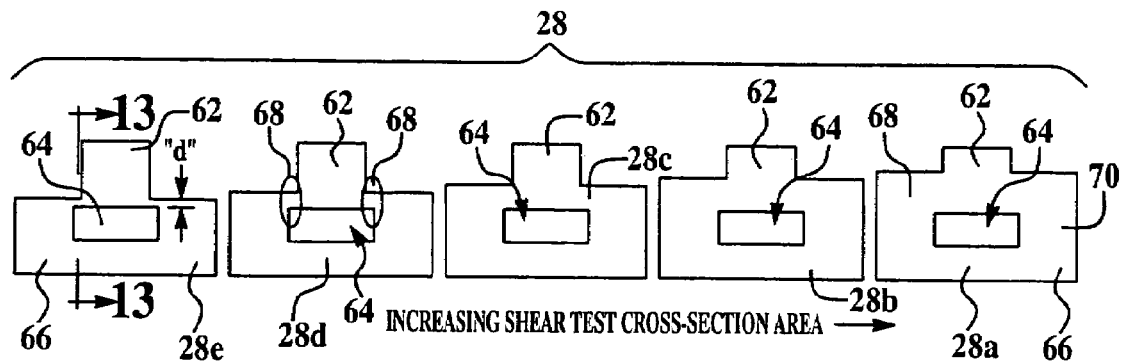
FIG. 12 is a front elevational view of another family of analytic forms shown in FIG. 1, useful in generating information relating to shear properties.
Figure 13:
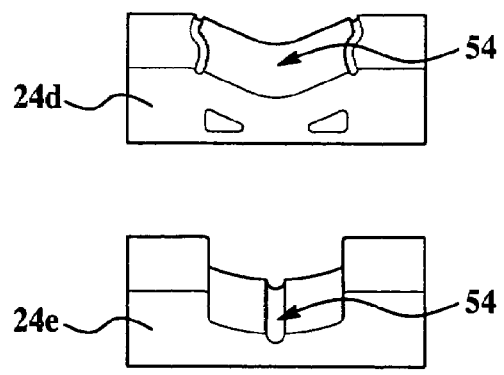
FIG. 13 is a sectional view taken along the line 13-13 in FIG. 12.

FIGS. 12 and 13 show further details of the family 28 comprising forms 28a-28e. Family 28 provide empirical data relating to the shear properties of the material which may be important in designing manufactured parts such as webs forming portions of beams. Each of the analytic forms 28a-28e include a base 66, a pair of spaced apart columns 70 that support a structural element in the form of a bridging portion 62 which overlies a central open area 64. The bridging material 62 is connected to the column 70 by a structural feature 68 having a thickness "d" which forms the test cross sectional area. The geometric arrangement of the analytic forms 28a-28e essentially eliminates bending resistance, leaving shear resistance as the only substantial mechanism to prevent failure. The pair of structural features 68 provides two test target cross sections that are subjected to shear stress in proportion to the bridging mass 62, and the dimensions of the test cross section. The dimension "d", and thus the shear test cross sectional area increases progressively from form 28e to form 28a.

Figure 14:
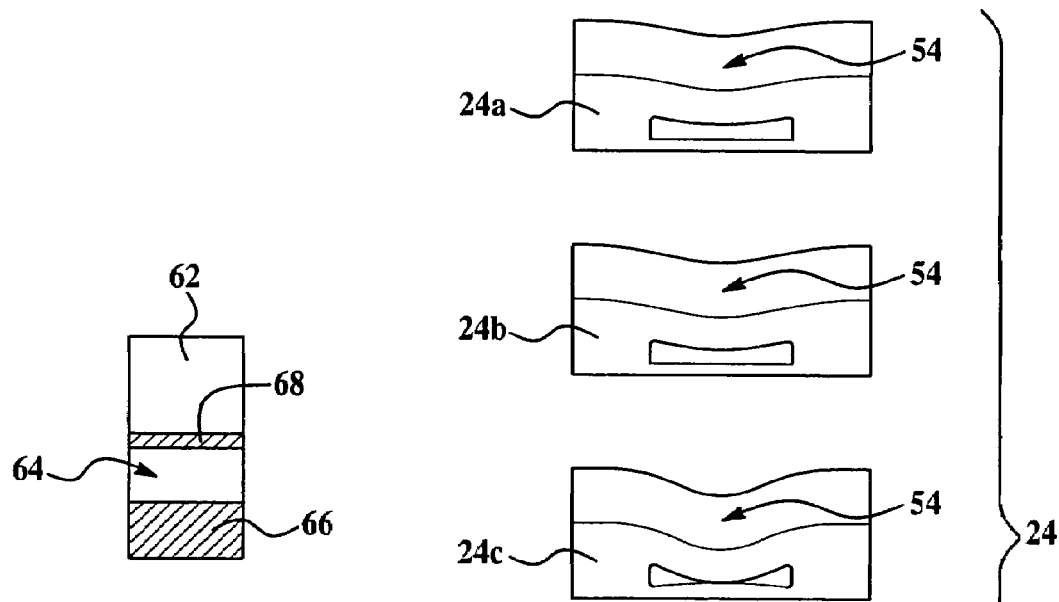
FIG. 14 is a perspective view of a family of analytic forms shown in FIG. 1, depicting progressive sagging of a feature as a result of the sintering process.

A variety of tests can be performed on the analytic forms to measure the various mechanical properties of the material discussed above. FIG. 14 shows a family 24 of analytic forms 24a-24e which have been subjected to processing, including sintering. As is apparent from FIG. 14, the bridging mass 54 which forms a structural feature of progressively thicker dimension shows slight sagging in forms 28a, 28b, but completely collapse and therefore fail in the case of forms 24c-24e.

Although this invention has been described with respect to certain exemplary embodiments, it is to be understood that the specific embodiments are for purposes of illustration and not limitation, as other variations will occur to those of skill in the art.

What is claimed is:

1. An analytical tool for use in analyzing a manufacturing process for producing powder metal parts, comprising:
at least a first family of powder metal forms produced by the manufacturing process, the forms in the first family being respectively subjected to different levels of stress during the manufacturing process and providing at least a first set of data predictive of mechanical properties of the powder metal parts produced by the manufacturing process;
wherein the powder metal forms each comprise a differing cross sectional area, said cross sectional area comprising a stress test area, and each of the forms includes a mass having a predetermined value imposing said differing levels of stress through the cross sectional area of the associated form.

2. The analytical tool of claim 1, wherein:
each of the forms includes a column, and the cross sectional areas of the respective columns are different.

3. The analytical tool of claim 1, wherein:
each of the forms includes a bridge and two columns respectively supporting the opposite ends of the column, and the cross sectional areas of the bridges are different.

4. The analytical tool of claim 3, wherein the cross sectional area of each of the bridges is subjected to shear stress.

5. The analytical tool of claim 3, wherein the cross sectional area of each of the bridges is subjected to bending stress.

6. The analytical tool of claim 1, wherein each of the forms includes a support and said mass supported by and overhanging the support, the mass including said cross sectional area subjected to bending stress and shear stress.

7. The analytical tool of claim 1, wherein each of the forms includes a support and said mass suspended from the support, the support having said cross sectional area subjected to tension stress by the mass.

8. The analytical tool of claim 1, wherein each of the forms comprises:
said mass having about the same predetermined value,
wherein the structural feature and the mass singularize the directional effect of gravity through the cross sectional area, said gravity comprising a load on said mass to produce said stress.

9. The analytical tool of claim 1, further comprising at least a second family of powder metal forms produced by the manufacturing process, the forms in the second family being respectively subjected to different levels of stress during the manufacturing process and providing a second set of data predictive of mechanical properties of the powder metal parts produced by the manufacturing process different than the mechanical properties predicted by the first set of data.

* * * * *